US008031339B2

(12) United States Patent
Steele

(10) Patent No.: US 8,031,339 B2
(45) Date of Patent: Oct. 4, 2011

(54) PARTICLE MEASUREMENT SYSTEMS AND METHODS

(75) Inventor: Paul T. Steele, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 105 days.

(21) Appl. No.: 12/335,408

(22) Filed: Dec. 15, 2008

(65) Prior Publication Data
US 2009/0262334 A1 Oct. 22, 2009

Related U.S. Application Data

(60) Provisional application No. 61/016,031, filed on Dec. 21, 2007.

(51) Int. Cl.
*G01N 15/02* (2006.01)
(52) U.S. Cl. .......... 356/336; 356/28.5; 356/338; 356/73
(58) Field of Classification Search .......... 356/335–343, 356/73, 28.5
See application file for complete search history.

(56) References Cited

U.S. PATENT DOCUMENTS

| | | | | |
|---|---|---|---|---|
| 4,483,614 A * | 11/1984 | Rogers | ........................ | 356/28.5 |
| 4,927,268 A * | 5/1990 | Carr et al. | ...................... | 356/336 |
| 4,948,257 A * | 8/1990 | Kaufman et al. | ............. | 356/521 |
| 5,192,870 A | 3/1993 | Batchelder et al. | | |
| 5,231,463 A * | 7/1993 | Shambaugh | .................. | 356/336 |
| 5,416,580 A * | 5/1995 | Trainer | ......................... | 356/336 |
| 5,481,357 A * | 1/1996 | Ahsan et al. | .................. | 356/338 |
| 5,502,561 A * | 3/1996 | Hutchins et al. | .............. | 356/336 |
| 7,260,483 B2 | 8/2007 | Gard et al. | ...................... | 702/22 |
| 7,471,393 B2 * | 12/2008 | Trainer | ......................... | 356/336 |
| 2005/0028577 A1 | 2/2005 | Chang et al. | | |
| 2008/0221814 A1* | 9/2008 | Trainer | ........................ | 702/70 |
| 2009/0002705 A1* | 1/2009 | Sharpe | ......................... | 356/338 |

FOREIGN PATENT DOCUMENTS

GB 2 242 021 A 9/1991
WO WO 2004/008110 A2 1/2004

OTHER PUBLICATIONS

Black, D.L., M.Q. McQuay et al., "Laser-based techniques for particle-size measurement: A review of sizing methods and their methods and their industrial applications." Progress in Energy and Combustion Science 22(3): 267-306, 1996.

Schmid, O., E. Karg et al., "On the effective density of non-spherical particles as derived from combined measurements of aerodynamic and mobility equivalent size." Journal of Aerosol Science 38(4): 431-443, 2007.

Wang, H.C. and W. John, "Particle Density Correction for the Aerodynamic Particle Sizer" Aerosol Science and Technology 6(2): 191-198, 1987.

(Continued)

*Primary Examiner* — Hoa Pham
(74) *Attorney, Agent, or Firm* — Eddie E. Scott; James S. Tak

(57) ABSTRACT

A system according to one embodiment includes a light source for generating light fringes; a sampling mechanism for directing a particle through the light fringes; and at least one light detector for detecting light scattered by the particle as the particle passes through the light fringes. A method according to one embodiment includes generating light fringes using a light source; directing a particle through the light fringes; and detecting light scattered by the particle as the particle passes through the light fringes using at least one light detector.

36 Claims, 4 Drawing Sheets

OTHER PUBLICATIONS

Geoffrey A. W. and B. James, "Design considerations and signal processing algorithms for laser-induced fluorescence airborne pathogen sensors" Proc. SPIE 5617, 1., 2004.

Hong, N. S., and Jones, A.R., "A light scattering technique for particle sizing based on laser fringe anemometry" J. Phys, D: Appl. Phys., vol. 9, 1976. Printed in Great Britain. 1976.

International Search Report and Written Opinion from PCT Application No. PCT/US2008/086955 mailed on Aug. 24, 2010.

Stevenson et al., "A laser velocimeter utilizing laser-induced fluorescence," Applied Physics Letters, vol. 27, No. 7, Oct. 1, 1975, abstract only.

* cited by examiner

FIG. 3

PARTICLE MEASUREMENT SYSTEMS AND METHODS

RELATED APPLICATIONS

This application claims priority to provisional U.S. application Ser. No. 61/016,031 filed on Dec. 21, 2007, which is herein incorporated by reference.

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to particle measurement, and more particularly to systems and methods for more efficient particle measurement.

BACKGROUND

Properties of small particles, such as size, density and fluorescence, are critical for many applications, but the small size makes measurement difficult. A potentially lethal anthrax spore, for example, has a diameter of one thousandth of a millimeter, a mass of one trillionth of a gram, and is completely invisible to the naked eye. Nonetheless, if anthrax spores were to suddenly appear in a subway it is clearly important to rapidly and accurately detect them. This is a significant challenge. Different applications have different requirements, but the more information an instrument can provide about the particles, the better. Similarly, the speed and accuracy of virtually any such instrument should be maximized while the size, cost and complexity are kept to a minimum. It would thus be desirable to provide a system and method having the ability to measure multiple particle properties more accurately and rapidly than known commercial instruments yet having the potential to be made smaller and more inexpensively.

Particle detection and analysis continue to evolve. One approach uses particle velocity. When a gas travels though a properly designed pressure gradient, entrained particles are focused and accelerated to a terminal velocity dependent upon their aerodynamic diameter. Measurement of the subsequent particle velocity is thus a means to obtain accurate aerodynamic particle size data. This basic technique has been employed for some time in a range of instruments. The velocity is generally determined by measuring the time it takes for a particle to pass between two laser beams separated by a known distance. Because of noise and finite clock speed, velocity is determined most accurately when the spacing (and hence transit time) between laser beams is large. As the mean spacing between particles becomes comparable to the spacing between lasers, however, the system becomes increasingly confused by coincident particles, crossing particles and related phenomena. Unfortunately, high particle loads must be dealt with in many applications. To handle such loads the lasers can be moved closer together (reducing sizing accuracy) or more lasers can be used (increasing cost). The Aerodynamic Particle Sizer (APS) from TSI is an example of an instrument in which two lasers are put close together to enable high analysis rates with rather low accuracy. The Aerosol Time of Flight Mass Spectrometer (ATOFMS) from TSI is a system in which two lasers are relatively far apart, which enables accurate sizing but a low analysis rate. The BioAerosol Mass Spectrometry (BAMS) system developed at LLNL uses six lasers to achieve both high accuracy and a high analysis rate, but the system is complex and expensive.

Therefore, it would be desirable to determine aerodynamic size and trajectory with high accuracy and speed but with minimal complexity and cost.

The aerodynamic size of a particle is related both to its physical size and to its density. The relative importance of the physical and aerodynamic sizes vary from application to application, but measuring both of them simultaneously would be useful in that it provides information on the particle's mass density, which may be very useful. As with the aerodynamic size, many techniques and instruments have been developed to measure physical size. Optical techniques include measuring the total amount of light scattered from a particle, the spatial pattern of scattered light and other scattered light properties, but very few techniques measure both sizes simultaneously. At least a few instruments, such as the APS, ATOFMS and BAMS, are in theory capable of making such measurements, but generally in these instruments the physical size measurement is rather inaccurate being based upon the total amount of light scattered from a particle in a laser beam.

Therefore, it would be desirable to determine the aerodynamic size, physical size and consequently mass density with higher accuracy and speed but with minimal complexity and cost.

Single particle fluorescence has been measured in several ways. The Hach Homeland Security Technologies BioLert system measures single particle fluorescence with a single continuous wave (CW) laser and minimal collection optics. The fluorescence signal produced and detected is very weak and accurate quantification is a challenge. The system is, however, relatively inexpensive. General Dynamic's Biological Agent Warning System (BAWS) uses a randomly-fired, pulsed laser to deposit more energy into a particle, which does produce more fluorescence, but cost is increased. The BAMS system uses an even more powerful pulsed laser triggered by a separate tracking system and carefully designed optics to collect as much fluorescence as possible, but the result is a very expensive system. Other fluorescence systems exist as well.

Therefore, where desired, it would be desirable to determine a particle's fluorescence with high accuracy and speed but with minimal complexity and cost.

SUMMARY

A system according to one embodiment includes a light source for generating light fringes; a sampling mechanism for directing a particle through the light fringes; and at least one light detector for detecting light scattered by the particle as the particle passes through the light fringes.

A method according to one embodiment includes generating light fringes using a light source; directing a particle through the light fringes; and detecting light scattered by the particle as the particle passes through the light fringes using at least one light detector.

Other aspects and embodiments of the present invention will become apparent from the following detailed description, which, when taken in conjunction with the drawings, illustrate by way of example the principles of the invention.

BRIEF DESCRIPTION OF THE DRAWINGS

FIG. 3 illustrates a size distribution of ambient aerosol particles at San Francisco International Airport (SFO) and a size distribution of particles aerosolized from a solution of *Bacillus atrophaeus* spores at Lawrence Livermore National Laboratory (LLNL).

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

Figure 4:
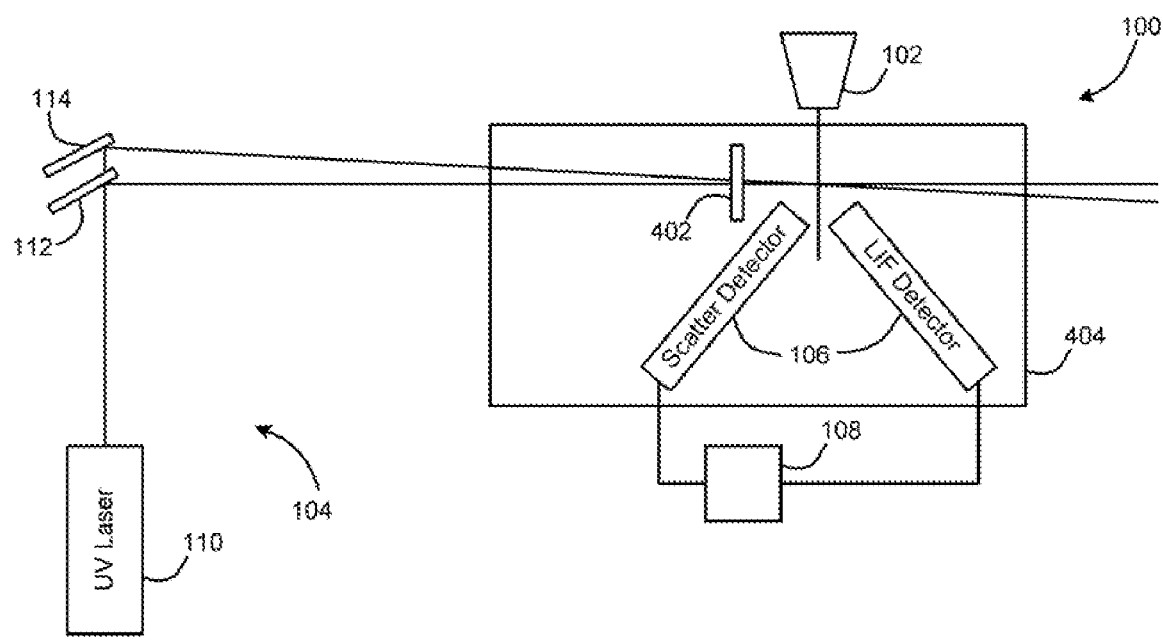
FIG. 4 is a schematic diagram of a system according to one embodiment.

Various embodiments of the present invention have the potential to simultaneously determine the trajectory, size, laser induced fluorescence and/or a quantity indicative of mass density of individual particles at a high rate. Illustrative advantages of various embodiments relative to existing instruments capable of measuring any of these properties are the simplicity of the physical hardware, the ability to perform all of the measurements simultaneously on a single particle and the speed, sensitivity and accuracy of measurement. Measurement of particle trajectory is integral to the operation of the device, but the other measurements could easily be removed to reduce size and cost. The analyzed particles may be in a vacuum (such as in a vacuum chamber 404, as shown in FIG. 4), gas, fluid or solid, but each scenario may require a unique configuration and in some applications not all measurements may be possible. Applications of various embodiments range from rapid detection of aerosolized biowarfare agents to environmental research and beyond. Furthermore, the ability to measure particle trajectory allows some embodiments of the present invention to be used as the "front end" of a device incorporating additional instrumentation, which enables many additional applications.

In one general embodiment, a system comprises a light source for generating light fringes; a sampling mechanism for directing a particle through the light fringes; and at least one light detector for detecting light scattered by the particle as the particle passes through the light fringes.

In one general embodiment, a method comprises generating light fringes using a light source; directing a particle through the light fringes; and detecting light scattered by the particle as the particle passes through the light fringes using at least one light detector.

As noted above, some embodiments of the present invention enable measurement and/or determination of properties of the particles such as the physical size, aerodynamic size, velocity, trajectory, fluorescence and/or density of individual aerosol particles.

Aerodynamic Size and Trajectory:

As noted above, when a gas travels though a properly designed pressure gradient, entrained particles are focused and accelerated to a terminal velocity dependent upon their aerodynamic diameter. (The aerodynamic diameter of a particle is equivalent to the physical diameter of a unit density sphere that displays identical aerodynamic behavior.) Measurement of the subsequent particle velocity is thus a means to obtain accurate aerodynamic particle size data.

Embodiments of the present invention provide less complex and more economical alternatives to the systems described above while simultaneously having potential for higher accuracy and analysis speed, as will soon become apparent. As will be described, light fringes, e.g., of an interference pattern or other periodic or nonperiodic spatial intensity modulation, may be formed through which the sampled particles pass. Each fringe, e.g., of the interference pattern, then acts essentially like a separate light beam. As a particle travels through the fringes, it will scatter light when within a fringe, and it will not scatter when between fringes (or will at least scatter less). The rate at which the scattered light flickers is thus a direct indication of the particle speed. Because the fringes are numerous, and have a known spacing especially where the light fringes include a spatially periodic pattern of light, the critical velocity measurement can be conducted in the frequency domain as opposed to the direct temporal domain. This has a number of advantages. For example, the accuracy of the velocity measurement is no longer directly limited by the finite clock speed. Second, noise can be much more effectively dealt with. This ultimately means that the fringe spacing may be made very small, enabling measurement of high particle concentrations, while maintaining high size accuracy and low cost. In this context, measurement of the particle size and trajectory are basically synonymous since both depend primarily upon the measurement of the particle velocity. Laser fringes have been used to measure particle velocity previously but not for these purposes, as far as the inventor is aware. Laser fringes have also been used to measure the physical particle size, but this is distinct from the aerodynamic size.

Fluorescence:

Single particle fluorescence can be measured in several ways in various approaches. One illustrative approach allows "lock-in" detection of fluorescence using a low cost CW laser or other light emitter. The fluorescence from a particle passing through a series of light fringes will flicker at the same frequency as the scattered light. Since the amount of light scattered from a particle generally exceeds the amount of fluorescence by orders of magnitude, the scattered light signal is relatively easily detected. In most fluorescence systems, a scattered light signal essentially tells the fluorescence detector where to look in time for the weak and easily missed fluorescence signal. In the present approach, the scattered light signal performs this duty, but it can also tell the fluorescence detector where to look in frequency space for the fluorescence signal. This allows sensitive detection of small signals and efficient rejection of noise. Spurious sources of background fluorescence or even just scattered light plague most known fluorescence detectors. However, in most embodiments, these interfering sources of noise will be well separated in the frequency domain from the signal of interest. For example, in embodiments using a CW laser, almost all of these interfering sources of noise will be CW.

Density:

A physical size of the particle may be determined using known methods. For example, bigger particles tend to scatter more light than smaller particles, and the total amount of scattered light is easily measured. Unfortunately this amount is influenced by other properties such as the particle's index of refraction, which reduces the sizing accuracy for arbitrary particles. As another example, the relative amount of light scattered in different directions can indicate particle size, but this is influenced by other factors as well. As yet another example, the physical size can be estimated by looking at a particle flicker as it passes through all interference pattern; small particles show a significant change in scattered light intensity as they move from fully in a fringe to fully between. These changes become less pronounced for larger particles, which can only be partly contained within a single fringe or dark spot. There are other methods as well, but these three in particular are mentioned because they may be employed separately or in any combination in the various embodiments of the present invention. Different factors influence the measurements differently, so performing multiple measurements allows a more accurate physical size to be determined and consequently a more accurate density.

Figure 1:
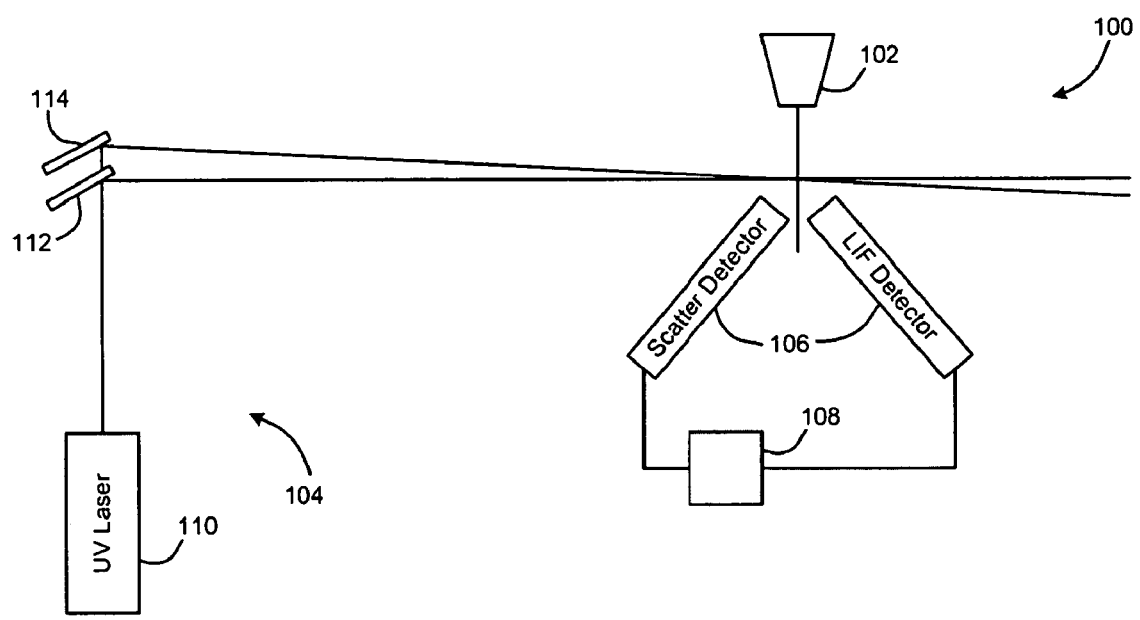
FIG. 1 is a schematic diagram of a system according to one embodiment.

System:

Systems according to some embodiments may measure the physical size, aerodynamic size, velocity, trajectory, fluorescence and/or density of individual aerosol particles. Referring to FIG. 1, a system 100 according to one general embodiment of the present invention includes a sampling mechanism 102, a light source 104, one or more light detectors 106 and a processing system 108 for data acquisition and analysis.

The sampling mechanism directs sample particles toward light fringes generated by the light source. The light source generates light fringes, e.g., a periodic spatial modulation of light intensity, through which the particles pass. The light source may optionally produce ultraviolet light to stimulate particle fluorescence. The detectors temporally and optionally spatially resolve the light scattered or emitted from the particles. The electronics then acquire and analyze data from the detectors to extract the various measurable particle properties.

Sampling Mechanism 102:

The type of sampling mechanism usable with each of the various embodiments is not critical, and any type of sampling mechanism capable of directing a particle through the light fringes can be used. Illustrative sampling mechanisms for use with particles in air include orifices, converging nozzles, aerodynamic focusing lens stacks, etc. Basically any small orifice across which a pressure differential can be created will work to some extent. In a proof-of-concept device, pressurized air with entrained particles was blown through a glass pipette. Moreover, the inlets for the BAWS, BioLert, APS, ATOFMS and SPAMS systems may also be used.

Similarly, many technologies exist for sampling and manipulating fluids such as gases or liquids with entrained particles. For example, a fluid with entrained particles may be passed through a transparent or translucent tube, between sheets of glass, etc. Moreover, the fluid may be passed through open space through the light fringes.

In particularly preferred embodiments, the inlet focuses the sampled particles into a narrow stream and imparts each particle with a velocity dependent upon its aerodynamic size. This last trait is typically only used for the aerodynamic size and density measurements, and is not otherwise critical for instrument operation.

Mechanisms for passing or rastering transparent solids with incorporated particles past the analysis region may also be implemented in the system.

Light Source 104:

The light source may include any type of suitable light emitter capable of creating light fringes. Illustrative light emitters include lasers, light emitting diodes, incandescent bulbs, fluorescent bulbs, etc. If there is no desire to generate or measure fluorescence, virtually any wavelength of light can be used.

The light source may also include mirrors, beam splitters, lenses, masks, etc. to aid in formation of the light fringes. Accordingly, only a single light emitter is needed, though some embodiments may have more than one light emitter.

As illustrated in FIG. 1, the light source may include an ultraviolet (UV) laser 110 that is split with a 50/50 beam splitter 112 and then made to interfere with itself, e.g., crossed, at the particle stream using a mirror 114. Alternatively, multiple mirrors could be used to fold the laser back upon itself (e.g., after it has passed under the sampling mechanism) to produce a similar interference pattern but with twice the laser power incident upon the particles. Microlenses or physical masks 402 (FIG. 4) may be used in other approaches to produce acceptable spatial modulations as well. Interference fringes are particularly easy to produce, however, and are particularly well suited for this application. The interference fringes may be oriented perpendicular to the particle stream along which the particles travel. However, the interference fringes can be oriented at some other angle.

Figure 2:
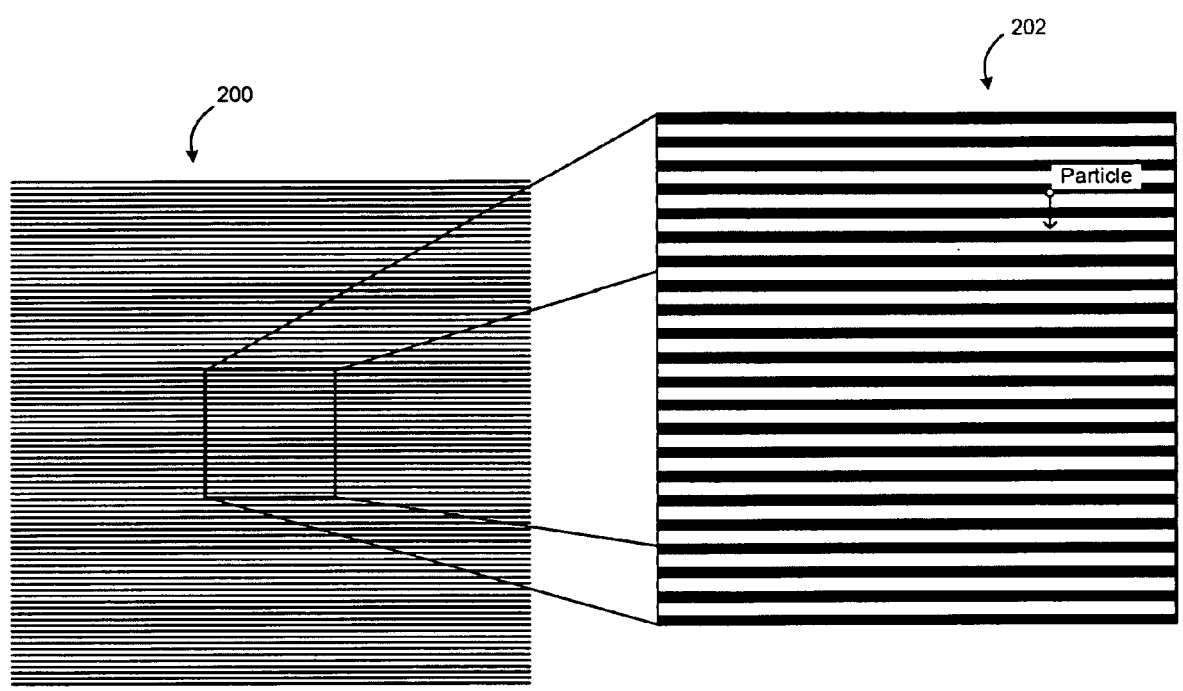
FIG. 2 is an image of the fringes produced in a proof-of-concept device according to one embodiment.

A representation 200 of the fringes produced in a proof-of-concept device is shown on the left hand side of FIG. 2. An enlargement 202 of the encircled region is shown on the right hand side of FIG. 2. The particles essentially flicker as they pass through the fringes. The periodic spatial intensity modulation is thus transformed into a periodic temporal modulation in the various optical signals generated and detected. This is a core phenomenon which sets this device apart from most instruments performing similar measurements. It allows the produced signals to be isolated both in time and frequency enabling efficient noise rejection, high sensitivity and high analysis rate.

Detectors 106:

A variety of optical detectors and associated data acquisition and analysis electronics may be used in various embodiments. Illustrative types of detectors include scatter detectors, fluorescence detectors, etc. Specific, illustrative detectors may include, photomultiplier tubes (PMTs), channel multiplier tubes (CMTs), photodiodes, microchannel plates (MCPs), etc. Known detectors may be used.

If particle tracking and sizing is performed with a UV laser, then fluorescence can be probed simultaneously. In one approach, Laser Induced Fluorescence (LIF) is collected with an ellipsoidal mirror and focused onto one or more appropriately filtered fluorescence detectors.

One challenge in collecting fluorescent signals has historically been dealing with a low signal-to-noise ratio. Embodiments of the present invention overcome this. Because the particles are periodically excited as they travel through light fringes, such as a sinusoidal interference pattern, the resulting fluorescence signals may be efficiently isolated in frequency space. Better rejection of noise enables better particle differentiation and quantification.

Processing System 108:

A processing system may optionally be coupled to the light detectors for performing data analysis via appropriate logic, software, etc. The data analysis may include such things as determining a property of the particle. The processing system may include onboard electronics, external hardware, output devices, input devices, memory and data storage devices, networking devices, etc. In a proof-of-concept device, photomultiplier tubes (PMTs) were used in combination with an oscilloscope and subsequent processing of the data was performed with a standard desktop computer. Another embodiment integrates dedicated data acquisition systems for digitizing the PMT outputs, a series of digital signal processors (DSPs) or field-programmable gate arrays (FPGAs) to process the raw data to the point where the relevant particle properties are easily extracted, and a computer or other processing device or system, which may be integral or external to the system. The computer may perform final processing of the data and store the results. In many applications, the computer may run additional software taking the particle properties as input and producing some desired output; for example, if the application involves bioaerosol detection, the properties of many particles may be fed into an alarm algorithm that ultimately indicates whether any bioaerosols are present. The computer may also optionally control and monitor hardware such as voltage supplies, lasers, pumps, etc. and provide a simple user interface.

Data Analysis:

A general method for determination of the various particle properties from the acquired signals according to one embodiment is presented below. Note that in any given implementation, additional, fewer, or alternate steps may be performed.

When a particle passes through the light fringes, it flickers at a specific frequency. This manifests itself as a strong peak in the power spectrum of the temporally resolved scattered light signal. This peak is easily identified and hence the frequency can be readily measured with high accuracy. The particle velocity is calculated as this frequency multiplied by the physical fringe spacing. When combined with the time at which the particle crosses the beam, the particle trajectory is thus fully determined.

Initial calculations indicate that it is possible to determine the velocity of a few micron particle crossing 10 micron fringes spread over a 300 micron region with an error of less than 0.1% using widely available optical detectors and electronics. This is comparable to the accuracy of the much larger BAMS tracking system.

Assuming that the sampling inlet has imparted the particle with a velocity characteristic of its aerodynamic diameter, the aerodynamic diameter may be determined from the velocity using a calibration curve empirically derived with standardized test particles. Since the time and frequency associated with the particle are known, any generated fluorescence signal can be easily extracted and separated from noise in the temporally resolved fluorescence detector signal. This constitutes "lock-in" fluorescence detection.

The aforementioned aerodynamic diameter is a function of particle size (or more specifically shape) and density. If an independent measure of the physical size (or shape) can be obtained then information on the density can be extracted. There are several known mechanisms to do this, which may be implemented in various approaches. One simple and crude method is to consider the magnitude of the total scattered light. Bigger particles generally scatter more light. An alternative is to consider the "visibility" or contrast ratio of the oscillations in the scattered light signal. A particle much smaller than the fringe spacing appears to oscillate in time from completely dark, when it is between fringes, to very bright when it is entirely within a fringe. The oscillations are less pronounced for larger particles, particularly where they cannot fit entirely within or between the fringes. Both of those methods are appealing in that all the necessary data is already acquired for the other measurements. An additional method to determine the particle size is to spatially resolve the scattered light signal. In an extreme form, this could be thought of as equivalent to determining the particle size with a microscope. This may require additional hardware but has potential for high accuracy.

Use of any of these approaches should enable the determination of an "effective" mass density. The resulting density is referred to as an "effective" density because it is likely to have some dependence upon the chemical and morphological properties of the particle as well as the true mass density. Nevertheless, this dependence may be very useful. It is not always the absolute accuracy of the measurement that is of importance but rather the ability of the measurement to differentiate particle types.

Any simple implementation of these strategies may result in a physical size estimate that has residual dependencies upon the optical properties of the particles and other factors. Thus the density or effective density estimate may show such dependencies as well. These dependencies may, however, be useful in certain applications and certainly do not render the measurement useless.

In one approach, the accuracy of the size and density measurements may be quantified with standard test particles (e.g. polystyrene latex spheres). Also, the ability of the correlated measurements to differentiate particles may be quantified by analyzing a range of relevant particle types (e.g. common background materials, known interferents and actual threat particles). Further more the results of the analysis can be stored in a library for later comparison to the field data being collected at that time. The particle being analyzed could then be identified based at least in part on such comparison.

The situation may arise in which the sampled particles do not have a velocity dependent upon their size, but rather have a fixed velocity. This may result if the particles are in a fluid or solid, or if the particles are very small and in a gas. Although this means that the aerodynamic diameter and density cannot be measured, it is advantageous in that the scattered signal itself can be detected with lock-in methods. This, for example, enables detection of particles much smaller than would otherwise be possible.

As already stated, the ability to isolate the various optical signals in time and frequency enables efficient noise rejection and high sensitivity. It also allows particles to be analyzed at rates that would completely saturate other instruments. Multiple particles can be in the light fringes simultaneously and yet separately analyzed, particularly where they have different velocities. This ability is very unusual, for example, in single particle fluorescence measurement.

Some of the proposed measurements can be performed independently with other instruments, but an integrated approach is more accurate and yields correlated results. In some approaches, the data analysis may be further expanded to include additional processing of the particle properties. As mentioned above, one example would be to examine the data from many particles to determine if a biological hazard were present. In other applications, the analysis might automatically report size or fluorescence distributions for test aerosols.

It should also be understood that the techniques presented herein might be implemented using a variety of technologies. For example, the methods described herein may be implemented in software running on a computer system, or implemented in hardware utilizing either a combination of microprocessors or other specially designed application specific integrated circuits, programmable logic devices, or various combinations thereof. In particular, methods described herein may be implemented by a series of computer-executable instructions residing on a storage medium such as a carrier wave, disk drive, or computer-readable medium. Exemplary forms of carrier waves may be electrical, electromagnetic or optical signals conveying digital data streams along a local network or a publicly accessible network such as the Internet. In addition, although specific embodiments of the invention may employ object-oriented software programming concepts, the invention is not so limited and is easily adapted to employ other forms of directing the operation of a computer.

Various embodiments can also be provided in the form of a computer program product comprising a computer readable medium having computer code thereon. A computer readable medium can include any medium capable of storing computer code thereon for use by a computer, including optical media such as read only and writeable CD and DVD, magnetic memory, semiconductor memory (e.g., FLASH memory and other portable memory cards, etc.), etc. Further, such software can be downloadable or otherwise transferable from one computing device to another via network, wireless link, non-volatile memory device, etc.

Additionally, some or all of the aforementioned code may be embodied on any computer readable storage media including tape, FLASH memory, system memory, hard drive, etc. Additionally, a data signal embodied in a carrier wave (e.g., in a network including the Internet) can be the computer readable storage medium.

In Use:

In one illustrative embodiment, a system generally configured as shown in FIG. 1 functions as a continuously operable, "detect to warn" bioaerosol sensor with a false alarm rate an order of magnitude or more lower than existing sensors utilizing laser-induced fluorescence. The device is capable of rapidly probing and measuring the correlated size, fluorescence and "effective" density of individual aerosol particles in the respirable size range (1-10 microns). The system may also "track" individual particles for subsequent correlated analysis using orthogonal techniques to obtain even lower false alarm rates.

The system may be carried by soldiers, first responders or anyone entering an environment where a biological release may occur. As soldiers advance into battle, for example, the system may potentially indicate in real-time whether an airborne threat is present and allow retreat or donning of protective equipment before inhalation of a lethal or infectious dose. Such a handheld system with the speed and sensitivity required to "detect to warn" and a low false alarm rate has unquestionable value in many additional situations.

Figure 3:
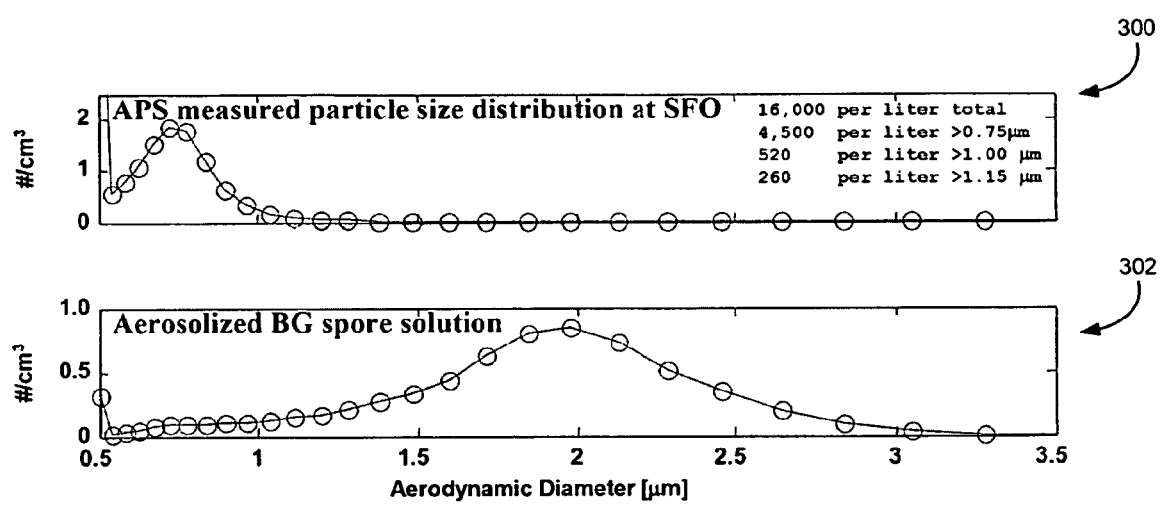

In important environments such as the San Francisco International Airport (SFO), the vast majority of ambient aerosol particles have a diameter of less than 1 micron. FIG. 3 shows a chart 300 of a particle size distribution taken at SFO, demonstrating that most particles taken in the sample have a diameter of less than 1 micron. This is not a size range of particular relevance for bioaerosols. An aerosol particle containing even a single spore or cell will generally be about 1 micron in diameter or larger.

There also seems to be a general consensus that one of the chief difficulties in producing an effective aerosol weapon is forming and dispersing a large quantity of very small particles; most particles are expected to be relatively large. Size could thus separate a large fraction of the natural background aerosol from potential bioagent aerosols and consequently lower the probability of false alarm. In the specific case of SFO, 16,000 particles per liter were observed on average with diameters greater than about 0.5 micron. Only 260 particles per liter had diameters in excess of 1.15 micron. Thus more than 98% of the background could have easily been rejected with only a very small drop in sensitivity to a release such as that shown in the lower chart 302 of FIG. 3, which depicts a size distribution of particles aerosolized from a solution of *Bacillus atrophaeus* spores at Lawrence Livermore National Laboratory (LLNL).

Density is expected to be a very useful quantity as well. The mass density of spores has been reported as falling between 1.29 and 1.45 g/cm$^3$. Cooking oils, fuel oils, gasoline and diesel generally have a mass density less than 1 g/cm$^3$ and are thought to be a common source of false alarms in some existing fluorescence detectors. Salts and other minerals generally have a density of 2 g/cm$^3$ or higher. Particles composed of such materials often compose a large fraction of the ambient aerosol. Mass density (or effective density as measured herein) is thus likely to differentiate a significant fraction of abundant background and interferent particles from true agent particles and consequently lower the probability of false alarm.

Preferably, at least three properties of the particle are measured simultaneously on a single particle and uniquely associated with that particle. By correlated, what is meant is that all measurements are performed on a single particle and associated with that specific particle (in contrast to a system where, for example, size is measured for one particle, fluorescence for another and density on yet another). Correlated measurements are much more useful than uncorrelated measurements.

The integration of fluorescence in differentiating particle types greatly enhances accuracy of results. Size, density and fluorescence may be measured simultaneously for each individual particle analyzed. Independent measurements of these quantities on different particles may be performed. Correlated single particle measurements, as performed here, are very useful. It is difficult, nonetheless, to predict the expected reduction in false alarm rate. Given the efficient rejection of background particles by size, the potential rejection of known interferents by density and the expected signal-to-noise improvement in the fluorescence measurement, an order of magnitude or greater reduction in false alarm rate relative to current detectors utilizing fluorescence alone seems probable. This claim is bolstered by BAMS data, which indicates that false alarms at SFO were not caused by biological particles and that speciation is not a necessity. In an environment where false alarms are caused by biological particles the reduction in false alarm rate would presumably be lessened.

Embodiments of the present invention may be integrated with or be readily coupled with additional instrumentation for various purposes, e.g., to further reduce false alarm rates. It could, for example, be incorporated into a next generation BioAerosol Mass Spectrometry (BAMS) system which would be smaller, cheaper, and more robust than current instruments, yet have equal or better performance. Given the relative infancy of the field of rapid bioaerosol detection, embodiments of the present invention may be well used to characterize pertinent environments just as the BAMS system has been used.

In further approaches, embodiments of the present invention may be used for environmental research apart from bioaerosol detection.

Examples of existing commercial instruments that could be readily replaced by the invention include particle sizers, single particle fluorescence detectors/analyzers, size and fluorescence analyzers, etc. Embodiments of the present invention are expected to be of roughly equal or lesser cost and size than these existing devices, yet have equal or superior performance.

Further applications of various embodiments include filter and air-cleaner testing, inhalation toxicology studies, indoor air-quality monitoring, biological aerosol investigations, drug delivery studies, atmospheric studies, ambient air monitoring, test-aerosol characterization, powder sizing, etc. This list is not exhaustive, and an even greater range of applications is expected.

While several of the aforementioned devices analyze particles in a gas, other applications are also anticipated. Flow cytometers are widely used to analyze particles in a fluid and could similarly benefit from embodiments of the present invention. Flow cytometers are utilized in fields including molecular, plant and marine biology and various medical fields such as pathology and immunology.

Many other combinations and resulting applications are possible

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A system, comprising:
    a light source for generating light fringes;
    at least one light detector for detecting light scattered by the particle as the particle passes through the light fringes; and
    a processing system coupled to the at least one light detector, the processing system being for determining an effective mass density of the particle based on an output of the at least one light detector.

2. The system of claim 1, wherein the light source includes at least one of a laser, a light emitting diode, and a bulb.

3. The system of claim 1, wherein the light fringes are spatially and temporally stationary.

4. The system of claim 1, wherein the light source includes a laser emitting ultraviolet light or other wavelengths capable of exciting fluorescence.

5. The system of claim 1, wherein the light source includes a beam splitter.

6. The system of claim 1, wherein the light source includes mirrors for folding light back on itself for generating the light fringes.

7. The system of claim 1, wherein the light source includes a mask.

8. The system of claim 1, wherein the light fringes are interference fringes.

9. The system of claim 1, further comprising a sampling mechanism for directing a particle through the light fringes.

10. The system of claim 1, wherein the processing system also determines at least one property of the particle selected from a group consisting of a velocity of the particle, a physical size of the particle, an aerodynamic size of the particle, a trajectory of the particle, and a fluorescence of the particle.

11. The system of claim 10, wherein at least three of the properties are measured simultaneously on a single particle and uniquely associated with that particle.

12. The system of claim 1, wherein the processing system includes logic or software embodied on a computer readable medium for discerning separate particles passing through the light fringes at the same time at different velocities.

13. The system of claim 1, wherein the at least one light detector includes a scatter detector.

14. The system of claim 1, wherein the at least one light detector includes a fluorescence detector.

15. The system of claim 1, wherein the particle passes through the light fringes in a vacuum chamber.

16. The system of claim 1, wherein the particle passes through the light fringes in a liquid.

17. The system of claim 1, wherein the particle passes through the light fringes in a transparent solid.

18. The system of claim 1, wherein the light fringes include a spatially periodic pattern of light.

19. A method, comprising:
    generating light fringes using a light source;
    directing a particle through the light fringes; and
    detecting light scattered by the particle as the particle passes through the light fringes using at least one light detector; and
    determining an effective mass density of the particle.

20. The method of claim 19, wherein the light source includes a laser.

21. The method of claim 19, wherein the light fringes are spatially and temporally stationary.

22. The method of claim 19, wherein the light source includes a laser emitting ultraviolet light.

23. The method of claim 19, wherein the light source includes a beam splitter.

24. The method of claim 19, wherein the light source includes mirrors for folding light back on itself for generating the light fringes.

25. The method of claim 19, wherein the light source includes a mask.

26. The method of claim 19, wherein the light fringes are interference fringes.

27. The method of claim 19, further comprising determining a property of the particle selected from a group consisting of a velocity of the particle, a physical size of the particle, an aerodynamic size of the particle, a trajectory of the particle, and a fluorescence of the particle.

28. The method of claim 27, wherein multiple particles are directed through the light fringes at a same time; and further comprising discerning the separate particles simultaneously passing through the light fringes and determining an effective mass density for each of the particles.

29. The method of claim 27, wherein at least three of the properties are measured simultaneously on a single particle and uniquely associated with that particle.

30. The method of claim 19, further comprising discerning the separate particles passing through the light fringes at different velocities.

31. The method of claim 19, wherein the at least one light detector includes a scatter detector.

32. The method of claim 19, wherein the at least one light detector includes a fluorescence detector.

33. The method of claim 19, wherein the particle passes through the light fringes in a vacuum chamber.

34. The method of claim 19, wherein the particles passes through the light fringes in a liquid.

35. The method of claim 19, wherein the particle passes through the light fringes in a transparent solid.

36. The method of claim 19, wherein the light fringes include a spatially periodic pattern of light.

* * * * *